United States Patent
Marin

(10) Patent No.: US 7,960,410 B2
(45) Date of Patent: *Jun. 14, 2011

(54) METHOD FOR TREATING INSULIN RESISTANCE, ABDOMINAL OBESITY, HYPERTENSION, HYPERINSULINEMIA, AND ELEVATED BLOOD LIPIDS WITH A CORTISOL INHIBITOR

(75) Inventor: Per Marin, Güteberg (SE)

(73) Assignee: Cortendo AB, Gothenburg (SE)

(*) Notice: Subject to any disclaimer, the term of this patent is extended or adjusted under 35 U.S.C. 154(b) by 338 days.

This patent is subject to a terminal disclaimer.

(21) Appl. No.: 11/223,074

(22) Filed: Sep. 10, 2005

(65) Prior Publication Data
US 2006/0014758 A1 Jan. 19, 2006

Related U.S. Application Data

(60) Division of application No. 10/654,809, filed on Sep. 4, 2003, which is a division of application No. 09/712,472, filed on Nov. 14, 2000, now Pat. No. 6,642,236, which is a division of application No. 09/211,282, filed on Dec. 14, 1998, now Pat. No. 6,166,017, which is a continuation of application No. 08/776,983, filed on Feb. 6, 1997, now Pat. No. 5,849,740, and a continuation of application No. PCT/SE94/00729, filed on Aug. 9, 1994.

(51) Int. Cl.
*A61K 31/445* (2006.01)
*A61K 31/56* (2006.01)
*A61K 31/415* (2006.01)

(52) U.S. Cl. ........ 514/315; 514/178; 514/396; 514/866; 514/909

(58) Field of Classification Search .................. 514/247, 514/178, 396, 467, 866
See application file for complete search history.

(56) References Cited

U.S. PATENT DOCUMENTS

| | | | |
|---|---|---|---|
| 4,466,978 A | 8/1984 | Naylor | |
| 4,491,588 A | 1/1985 | Rosenburg et al. | |
| 4,814,333 A | 3/1989 | Ravaris | |
| 4,871,741 A | 10/1989 | Gadebusch et al. | |
| 4,956,391 A | 9/1990 | Sapse | |
| 5,175,144 A | 12/1992 | Walser | |
| 5,432,176 A | 7/1995 | Walser | |
| 5,527,788 A | 6/1996 | Svec et al. | |
| 5,591,736 A | 1/1997 | Walser | |
| 5,849,740 A * | 12/1998 | Marin | 514/247 |
| 6,040,307 A | 3/2000 | Gray et al. | |
| 6,166,017 A * | 12/2000 | Marin | 514/247 |
| 6,274,582 B1 * | 8/2001 | Mårin | 514/254.1 |
| 6,428,809 B1 | 8/2002 | Abrams et al. | |
| 6,545,028 B2 | 4/2003 | Jensen et al. | |
| 6,642,236 B1 * | 11/2003 | Marin | 514/247 |
| 6,702,683 B2 | 3/2004 | Abrams et al. | |
| 6,846,800 B1 | 1/2005 | Johannsson et al. | |
| 6,881,739 B1 * | 4/2005 | Marin et al. | 514/254.01 |

OTHER PUBLICATIONS

Balbi et al., "Treatment of Ketoconazole in diabetic patients with vaginal candidiasis", Drugs Under Experimental and Clinical Research, vol. 12, No. 5, pp. 413-414 (1986), see enclosed abstract.*
Reich et al., "Rhinocerebral mucormycosis in a diabetic ketoacidotic patient", Jorunal of Neurology, vol. 232, No. 2, pp. 115-117 (1985).*
Sonino et al., "Ketoconazole treatment in Cushing's syndrome: experience in 34 patients", Clinical Endocrinology, vol. 35, No. 4, pp. 347-352 (Oct. 1991), see enclosed abstract.*
Pepper, G.M. et al, "Ketoconazole Reversed Hyperandrogenism . . . ," J. Clin. Endocrin. & Metab., 1987, vol. 65, No. 5, pp. 1047-1052.
Verhelst, J.A. et al., "Use of Ketoconazole in the Treatment of Virilizing Adrenocortical Carcinoma," ACTA Endocrin., 1989, vol. 121, No. 2, pp. 229-234.
Sonino, N., et al., "Ketoconazole treatment in Cushing's syndrome . . . ," Clin. Endocrin. 1991 United Kingdom, 1991, vol. 35, No. 4, pp. 347-352.
Krishnaiah, Y.S.R., et al., "Drug Interaction of tolbutamide with ketoconazole in diabetic rabbits," Indian J. Pharmacol., 1993, vol. 125, No. 3, pp. 146-148.
Brindley, D.N., et al., "Neuroendocrine regulation and obesity," Int'l J. Obesity 1992 United Kingdom, 1992, vol. 16, No. Suppl. 3, pp. S73-S79.
European Patent Office, European Search Report in respect of EP 03 01 2414, Aug. 4, 2003.
Paola Loli et al., "Use of Ketonconazole in the Treatment of Cushing's Syndrome," J. Clin. Endocrinology and Metabolism, vol. 63, No. 6, 1365-1371.
G.M. Pepper, "Ketoconazole Reverses Hyperandrogenism in a Patient with Insulin Resistance and Acanthosis Nigricans", J. Clin. Endo. & Metab., v. 66, No. 5, 1047-1052.
Viscera Obesity: A "Civilization Syndrome". Obesity Research, vol. 1 No. 3, May 1993.
A.T. Sapse, "Stress, Cortisol, Interferon and 'Stress' Diseases —1. Cortisol as the Cause of 'Stress' Diseases". Medical Hypotheses, vol. 13. pp. 31-44, 1984.
Bjorntorp, P., "Metabolic implications of body fat distribution," Diabetes Care 1991, 14(12):1132-1143.
Bjorntorp, P., "Regional fat distribution—implications for type II diabetes," Int J Obesity 1992, 16(4):S19-S27.
Brindley, D.N., "Role of glucocorticoids and fatty acids in the impairment of lipid metabolism," Int J Obesity 1995, 19(1):S69-S75.
Byrd et al., "Paecilomyces varioti pneumonia in a patient with Diabetes Mellitus," J. Diab Comp 1992, 6:150-153.

(Continued)

*Primary Examiner* — Kevin Weddington
(74) *Attorney, Agent, or Firm* — Bradley N. Ruben

(57) ABSTRACT

The invention concerns the use of ketoconazole and derivatives having a corresponding biological activity, and combinations thereof, in the treatment of abdominal obesity, hypertension, hyperinsulinemia, and elevated blood lipids.

40 Claims, No Drawings

OTHER PUBLICATIONS

Nichols, R., "Problems associated with medical therapy of Canine Hyperandrenocorticism," Problems in Veterinary Medicine, 1990, 2(4):551-556.

Peeke and Chrousos, "Hypercortisolism and obesity," Ann. New York Acad. Sci. 665-676.

Rotstein et al., "Stereoisomers of ketoconazole: Preparation and biological activity," J Med Chem 1992, 35:2818-2825.

A.T. Sapse, "Stress, Cortisol, Interferon and 'Stress' Diseases —I. Cortisol as the Cause of 'Stress' Diseases". Medical Hypotheses, vol. 13. pp. 31-44, 1984.

Siever, L.J et al., "Plasma Cortisol Response to Clonidine in Depressed Patients and Controls" Arch Gen Psychiatry, Jan. 1984, p. 63-68, vol. 41.

Phillips, P., et al.; "Adrenal Response to Corticotropin during Therapy with Itraconazole," Antimicrobial Agents and Chemotherapy, Apr. 1987, pp. 647-649.

Voet, D. and J. Voet, Biochemistry, 2nd Ed., 1995, Fig. 23-52 (Sect. 23-6), John Wiley & Sons, Inc. (New York).

Rang, H., et al., Pharmacology, 1995, pp. 421-422, Churchill Livingstone (New York).

* cited by examiner

METHOD FOR TREATING INSULIN RESISTANCE, ABDOMINAL OBESITY, HYPERTENSION, HYPERINSULINEMIA, AND ELEVATED BLOOD LIPIDS WITH A CORTISOL INHIBITOR

RELATED APPLICATIONS

This application is divisional of application Ser. No. 10/654,809, filed Sep. 4, 2003, which is a division of 09/712,472, filed Nov. 14, 2000, now U.S. Pat. No. 6,642,236, which is a division of application Ser. No. 09/211,282, filed Dec. 14, 1998, now U.S. Pat. No. 6,166,017, which is a continuation of application Ser. No. 08/776,983, filed Feb. 6, 1997, now U.S. Pat. No. 5,849,740, and a continuation of PCT/SE94/00729, filed Aug. 9, 1994, the disclosures of which are incorporated herein by reference.

The present invention relates to the use of ketoconazole or molecules resembling ketoconazole but with some side-chains, not affecting the biological activity compared to ketoconazole, changed for manufacturing drugs for treatment of diabetes mellitus type II.

The drug ketoconazole (e.g., under the Fungoral™ brand) is a well-documented drug for treatment of fungal infections. The process of making ketoconazole is well known and described. In this invention Fungora™ capsules aimed at oral administration should be used. This means that Fungoral™ should be administered the same way (oral) and in the same composition that is already well-known on the market for treatment of fungal infections the oral route. Therefor it is not considered necessary to further describe the process of making Fungoral™. For the same reason it is not considered necessary to give a full, clear, concise and exact term of this drug, since it is already well known for persons skilled in the art of medicine.

The drug comprising ketoconazole (e.g., under the Fungoral™ brand) and chemically closely related substances, the mode of operation of which is to influence the normal cortisol synthesis in the adrenal glands in such a way that the production of biologically perfectly acting cortisol is partly inhibited, is intended to be used for medical treatment of diabetes mellitus type II in men and women as well as for counteracting the risk factors which are parts of the Metabolic Syndrome (also known as "the deadly quartet" or "Syndrome X" or the "Insulin Resistance Syndrome"), which is characterised by an accumulation of risk factors for cardiovascular disease, stroke and diabetes mellitus type II, i.e. insulin resistance, hyperinsulinemia, abdominal obesity, (caused by an accumulation of intra-abdominal fat), elevated serum lipids, and raised blood pressure, as well as reducing the risk of development of these diseases.

In this new invention ketoconazole shall be administered the oral route in doses of 100-800 mg daily. The drug can be administered once or several times daily. At present a dose of 400 mg administered in the evening has been proven to be the best mode. However, we also claim that administration at other points of time, and in other doses (100-800 mg) can be equally effective.

Since ketoconazole is also inhibiting the normal production of testosterone in men, it is possible that this sex needs a certain amount of testosterone supplementation when treated with ketoconazole, to have an optimal effect of the treatment.

We have investigated a group of people with diabetes mellitus type II. They have been treated with ketoconazole during 2 and 6 weeks, respectively. Investigations before and after treatment have shown a decrease in blood glucose measured either in the fasting state or at 2 hours after an intravenous glucose infusion, and most important, a remarkable improvement of insulin sensitivity. More exact data from these studies are given in the tests described below. Since a decreased insulin sensitivity is a central part of "The metabolic syndrome", also known as "The deadly quartet", "Syndrome X" or the "Insulin Resistance Syndrome" we also claim that fungoral treatment to people with risk factors according to this syndrome should be expected to be effective also for treatment of these specific risk factors (abdominal obesity, hypertension, elevated blood lipids) as well as for decreasing the risk for diseases caused by these risk factors (Cardiovascular disease such as coronary artery disease, other arteriosclerotic manifestations including stroke).

The mechanism of the action of ketoconazole is that the substance influence the cortisol synthesis of the adrenal glands in such a way that a sub-fraction of a biologically non-perfect substance similar to cortisol, so called "crippled cortisol", is formed instead of the normal cortisol molecule.

The cortisol antagonistic effect of the drug is considered to have a central importance for the positive effects on the risk factors mentioned above, decreasing the metabolic activity of fat inside the abdominal cavity, which in turn leads to a decreased fat infiltration of the liver, improving the glucose homeostasis over the liver and peripherally in the tissues in turn leading to improvement of diabetes mellitus type II (decreasing blood glucose and increasing insulin sensitivity), reducing the serum lipids through improvement of the regulating mechanisms in the liver and also inhibiting cholesterol synthesis by a direct effect on the adrenal glands. A positive effect on the blood pressure can also be expected via the cortisol-antagonistic effect.

The scientific basis for these effects can be explained by an inhibition of the physiologically increased cortisol secretion rate that is known to be present under the conditions described above. (The metabolic syndrome and its synonyms described above). This increased cortisol secretion can per se explain all the parts of the syndrome described including the development of diabetes mellitus type II. The scientific explanation for the beneficial effects of ketoconazole on the treatment of diabetes mellitus type II is its effects of decreasing the secretion of biologically active cortisol.

The basic substance is ketoconazole in the chemical form which is known and well documented in the literature. This substance can be further chemically modified while maintaining the same biological effects by exchange of different molecular side chains. These substances similar to ketoconazole can then be expected to have similar and/or better effects on the cortisol inhibiting mechanism, which is described above.

A positive effect on the treatment of patients with diabetes mellitus type II with ketoconazole has been shown in that after the administration of ketoconazole a reduction of the insulin insensitivity (resistance), which is often associated with this disease, has been measured. This has been measured as an improved (i.e., reduced) insulin resistance measured with a so called euglychemic glucose clamp method. Thus, the examined patients have improved with regard to their diabetes, measured in the above described way, which in parallell also have resulted in lower blood glucose after treatment compared to before treatment.

The category of patients, that would have an especially good use of ketoconazole are patients with diabetes mellitus type II with insulin insensitivity and despite treatment with usual anti-diabetic drugs and/or insulin still have remaining elevated glucose values in the blood in fasting condition as well as after a meal. The investigated patients had decreased insulin sensitivity compared to healthy persons, measured by euglychemic glucose clamp. Supply of ketoconazole to this category of patients has been shown to have a positive and specific effect on the insulin insensitivity in such a way that their diabetes mellitus type II was improved. This was measured as improved insulin sensitivity and lower blood glucose.

Other positive effects have also been detected among these patients: Reduced cholesterol levels in the plasma as well as decreasing blood pressure values.

Results of Clinical tests of women with diabetes mellitus type II, treated with ketoconazole.

Group 1 consists of 3 patients (mean age: 46 years) treated with ketoconazole for 2 weeks, administered orally 22:00 in the evening in the dose of 400 mg.

Group 2 consists of 5 patients (mean age: 51 years) treated with ketoconazole for 6 weeks, administered orally 22:00 in the evening in the dose of 400 mg. Results are expressed as mean values within groups.

| Variables studied | Group 1 | | Group 2 | |
| --- | --- | --- | --- | --- |
| | Before t. | After t. | Before t. | After t. |
| Fasting blood glucose (mmol/L) | 10.20 | 8.77 | 7.20 | 7.10 |
| Blood glucose (mmol/L) 2 hours after start of an i.v. glucose in-fusion | 9.73 | 7.90 | 6.48 | 5.76 |
| GIR (glucose infusion rate during euglycemic glucose clamp expressed as mg glucose per minute divided by lean body mass), indicating insulin sensitivity | 0.9 | 1.85 | 2.97 | 4.32 |
| Fasting serum total cholesterol (mmol/L) | 5.80 | 5.67 | 4.80 | 4.10 |
| Systolic blood pressure (mm Hg) measured after 5 min. in supine position. 2 measurements averaged | 140 | 135 | 125 | 123 |
| Diastolic blood pressure (mm Hg) measured after 5 min. in supine position. 2 measurements averaged | 70 | 70 | 75 | 72 |
| Serum-ASAT (µkat/L) | 0.36 | 0.33 | 0.26 | 0.25 |
| Serum-ALAT (µkat/L) | 0.61 | 0.52 | 0.40 | 0.37 |

The foregoing description is meant to be illustrative and not limiting. Various changes, modifications, and additions may become apparent to the skilled artisan upon a perusal of this specification, and such are meant to be within the scope and spirit of the invention as defined by the claims.

What is claimed is:

1. A method for treating a patient, comprising:
   identifying a patient with metabolic syndrome, wherein said metabolic syndrome is characterized by a presence of the combination of insulin resistance, hyperinsulinemia, abdominal obesity, elevated serum lipids, and raised blood pressure; and
   administering to the patient for at least two weeks an amount of ketoconazole effective to treat metabolic syndrome in the patient by reducing the presence of at least one of said characteristics of metabolic syndrome.

2. A method for treating a patient, comprising:
   identifying a patient with metabolic syndrome, wherein said metabolic syndrome consists essentially of the combination of insulin resistance, hyperinsulinemia, abdominal obesity, elevated serum lipids, and raised blood pressure; and
   administering to the patient for a duration of at least two weeks an amount of ketoconazole effective for decreasing insulin resistance in the patient.

3. A method for treating a patient, comprising:
   identifying a patient having hyperinsulinemia, wherein said hyperinsulinemia is due to type II diabetes mellitus; and
   administering to the patient for a duration of at least two weeks an amount of ketoconazole effective to decrease said hyperinsulinemia and thereby treat type II diabetes mellitus in the patient.

4. A method for treating a human patient, comprising:
   identifying a human patient having an increased insulin resistance;
   identifying that the increased insulin resistance is part of a disorder that consists of type II diabetes mellitus; and
   administering to the human patient for a duration of at least two weeks an amount of ketoconazole effective to decrease insulin resistance.

5. A method for treating a human patient, comprising:
   identifying a human patient having increased insulin resistance;
   identifying that the increased insulin resistance is part of a disorder that consists of metabolic syndrome; and
   administering to the human patient for a duration of at least two weeks an amount of ketoconazole effective to decrease insulin resistance.

6. A method for treating a patient, comprising:
   identifying a patient having a hyperinsulinemia disorder that is part of a metabolic syndrome; and
   administering to the patient for a duration of at least two weeks an amount of ketoconazole effective to decrease hyperinsulinemia, thereby treating hyperinsulinemia in the patient.

7. A method for treating a patient, comprising:
   identifying a patient having type II diabetes mellitus;
   determining that an insulin treatment of said patient does not result in lowering an elevated level of blood glucose in the patient; and
   administering to the patient for a duration of at least two weeks an amount of ketoconazole effective to decrease insulin resistance in the patient, thereby treating the type II diabetes.

8. A method for treating a patient, comprising:
   identifying a patient having insulin resistance, wherein said insulin resistance is attributed to a disorder consisting of type II diabetes mellitus; and
   administering to the patient for a duration of at least two weeks a composition, wherein said composition comprises a single treatment for type II diabetes mellitus, wherein said treatment essentially consists of an amount of ketoconazole effective to decrease insulin resistance.

9. The method of claim 1, wherein the daily dose of ketoconazole effective to reduce the presence of at least one of said characteristics is an amount between about 100 mg and about 800 mg.

10. The method of claim 9, wherein about 400 mg of ketoconazole is administered to the patient in the evening.

11. The method of claim 1, wherein the patient is a male and said method further comprises providing testosterone and administering the testosterone in an amount effective to reduce any decrease in the patient's testosterone caused by administration of ketoconazole.

12. The method of claim 2, wherein the daily dose of ketoconazole effective to decrease insulin resistance is an amount between about 100 mg and about 800 mg.

13. The method of claim 12, wherein about 400 mg of ketoconazole is administered to the patient in the evening.

14. The method of claim 2, wherein the patient is a male and said method further comprises providing testosterone and administering the testosterone in an amount effective to reduce any decrease in the patient's testosterone caused by administration of ketoconazole.

15. The method of claim 3, wherein the daily dose of ketoconazole effective to decrease hyperinsulinemia is an amount between about 100 mg and about 800 mg.

16. The method of claim 15, wherein about 400 mg of ketoconazole is administered to the patient in the evening.

17. The method of claim 3, wherein the patient is a male and said method further comprises providing testosterone and administering the testosterone in an amount effective to reduce any decrease in the patient's testosterone caused by administration of ketoconazole.

18. The method of claim 4, wherein the daily dose of ketoconazole effective to decrease insulin resistance is an amount between about 100 mg and about 800 mg.

19. The method of claim 18, wherein about 400 mg of ketoconazole is administered to the patient in the evening.

20. The method of claim 4, wherein the patient is a male and said method further comprises providing testosterone and administering the testosterone in an amount effective to reduce any decrease in the patient's testosterone caused by administration of ketoconazole.

21. The method of claim 5, wherein the daily dose of ketoconazole effective to decrease insulin resistance is an amount between about 100 mg and about 800 mg.

22. The method of claim 21, wherein about 400 mg of ketoconazole is administered to the patient in the evening.

23. The method of claim 5, wherein the patient is a male and said method further comprises providing testosterone and administering the testosterone in an amount effective to reduce any decrease in the patient's testosterone caused by administration of ketoconazole.

24. The method of claim 6, wherein the daily dose of ketoconazole effective to decrease hyperinsulinemia is an amount between about 100 mg and about 800 mg.

25. The method of claim 24, wherein about 400 mg of ketoconazole is administered to the patient in the evening.

26. The method of claim 6, wherein the patient is a male and said method further comprises providing testosterone and administering the testosterone in an amount effective to reduce any decrease in the patient's testosterone caused by administration of ketoconazole.

27. The method of claim 7, wherein the daily dose of ketoconazole effective to decrease insulin resistance is an amount between about 100 mg and about 800 mg.

28. The method of claim 27, wherein about 400 mg of ketoconazole is administered to the patient in the evening.

29. The method of claim 7, wherein the patient is a male and said method further comprises providing testosterone and administering the testosterone in an amount effective to reduce any decrease in the patient's testosterone caused by administration of ketoconazole.

30. The method of claim 8, wherein the daily dose of ketoconazole effective to decrease insulin resistance is an amount between about 100 mg and about 800 mg.

31. The method of claim 30, wherein about 400 mg of ketoconazole is administered to the patient in the evening.

32. The method of claim 8, wherein the patient is a male and said method further comprises providing testosterone and administering the testosterone in an amount effective to reduce any decrease in the patient's testosterone caused by administration of ketoconazole.

33. The method of claim 1, wherein the duration is at least six weeks.

34. The method of claim 2, wherein the duration is at least six weeks.

35. The method of claim 3, wherein the duration is at least six weeks.

36. The method of claim 4, wherein the duration is at least six weeks.

37. The method of claim 5, wherein the duration is at least six weeks.

38. The method of claim 6, wherein the duration is at least six weeks.

39. The method of claim 7, wherein the duration is at least six weeks.

40. The method of claim 8, wherein the duration is at least six weeks.

* * * * *